US 6,537,075 B1

(12) United States Patent
Valero-Cuevas

(10) Patent No.: US 6,537,075 B1
(45) Date of Patent: Mar. 25, 2003

(54) DEVICE FOR DEVELOPING AND MEASURING GRASPING FORCE AND GRASPING DEXTERITY

(75) Inventor: Francisco J. Valero-Cuevas, 222 Upson Hall, Ithaca, NY (US) 14853

(73) Assignee: Francisco J. Valero-Cuevas, Ithaca, NY (US)

( * ) Notice: Subject to any disclaimer, the term of this patent is extended or adjusted under 35 U.S.C. 154(b) by 0 days.

(21) Appl. No.: 09/479,450

(22) Filed: Jan. 11, 2000

(51) Int. Cl.⁷ .............................................. G09B 19/00
(52) U.S. Cl. ...................................... 434/247; 434/258
(58) Field of Search ................................ 434/247, 258; 482/44, 45, 46, 47, 48, 49, 50

(56) References Cited

U.S. PATENT DOCUMENTS

| | | | | |
|---|---|---|---|---|
| 3,559,988 A | * | 2/1971 | Greenless | 272/83 |
| 3,756,594 A | * | 9/1973 | Goodwin | 482/47 |
| 3,782,719 A | * | 1/1974 | Kuhlman | 482/48 |
| 3,784,193 A | * | 1/1974 | Simjian | 482/147 |
| 3,807,729 A | * | 4/1974 | Sigma | 482/49 |
| 4,039,183 A | * | 8/1977 | Sakurada | 482/46 |
| 4,262,898 A | * | 4/1981 | Lee | 482/49 |
| 4,513,962 A | * | 4/1985 | Robson | 482/49 |
| 4,553,746 A | * | 11/1985 | Lee | 482/49 |
| 4,632,383 A | * | 12/1986 | Tsuzuki | 482/49 |
| 4,729,560 A | * | 3/1988 | Cho | 482/82 |
| 4,749,183 A | * | 6/1988 | Cho | 482/82 |
| 4,875,469 A | * | 10/1989 | Brooks | 601/40 |
| 5,147,256 A | * | 9/1992 | Silagy | 482/47 |
| 5,160,303 A | * | 11/1992 | Smith | 482/123 |
| 5,222,926 A | * | 6/1993 | Eggen | 482/49 |
| 5,297,541 A | * | 3/1994 | Hensey | 601/40 |
| 5,431,611 A | * | 7/1995 | Silagy | 482/47 |
| 5,445,582 A | * | 8/1995 | Brown | 482/48 |
| 5,643,161 A | * | 7/1997 | Gordon | 482/127 |
| 5,690,585 A | * | 11/1997 | Ditsch | 482/47 |
| 5,720,700 A | * | 2/1998 | Buoni | 482/124 |
| 5,738,613 A | * | 4/1998 | Clayton | 482/47 |
| 5,769,758 A | * | 6/1998 | Sarkinen | 482/44 |
| 6,099,438 A | * | 8/2000 | Dawson | 482/47 |

* cited by examiner

Primary Examiner—Derris H. Banks
Assistant Examiner—Kurt Fernstrom
(74) Attorney, Agent, or Firm—Lumen Intellectual Property Services, Inc.

(57) ABSTRACT

A hand-held compressible and expandable device is used to develop and measure the persons grasping strength and grasping dexterity. The device in preferably compressed and/or expanded by the user's digits. Preferably, the device is both compressible and flexible so that the user must provide a linearly or controlled force to compress the device successfully. In one embodiment, the device has a spring that is both compressible and flexible. One end of the spring has a finger pad and at the other end a thumb pad. The ability of the user to compress the spring between the finger and the thumb gauges the users grasping strength, while the ability of the user to compress the spring in a linear fashion provides a measure of the user's dexterity. The device also can be configured to automatically count the number of successful and/or unsuccessful compressions mechanically, optically or electrically. The compressibility, flexibility and difficulty of use of the device is modified using a variety of mechanisms besides modifying the stiffness, diameter, length or other properties of springs including rubbers, foam rubber elements and hinges. The device is particularly useful to provide a low cost diagnosis and therapy for patients and individuals that need to develop or regain grasping strength and dexterity.

30 Claims, 14 Drawing Sheets

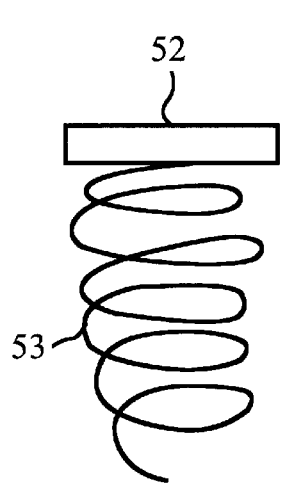
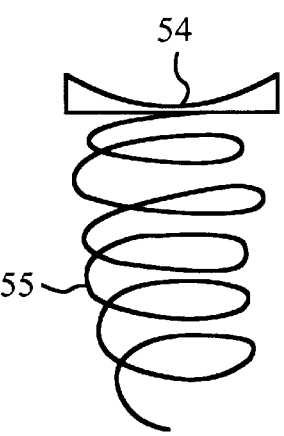
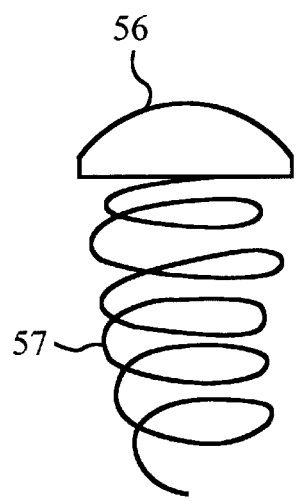
*FIG. 5A*     *FIG. 5B*     *FIG. 5C*
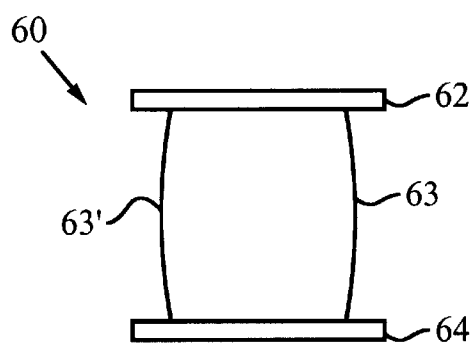
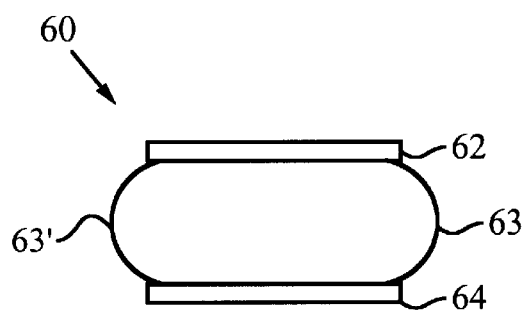
*FIG. 6A*     *FIG. 6B*
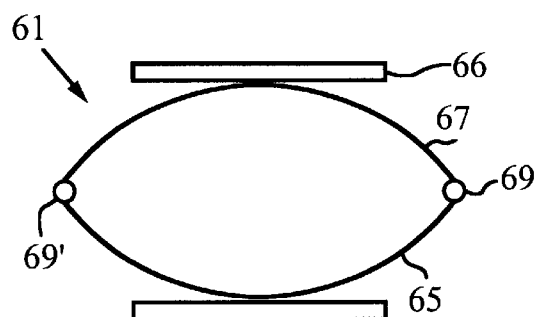
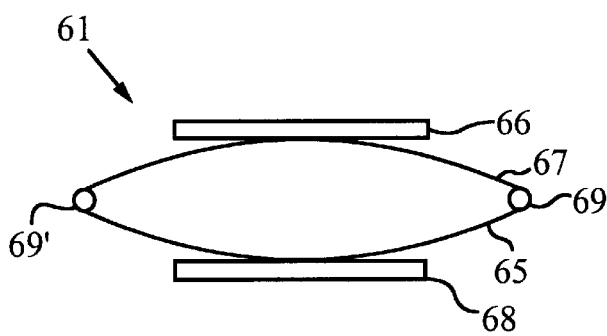
*FIG. 7A*     *FIG. 7B*

DEVICE FOR DEVELOPING AND MEASURING GRASPING FORCE AND GRASPING DEXTERITY

FIELD OF THE INVENTION

This invention relates generally to devices for developing and measuring grasping force and grasping dexterity. In particular, it relates to compressible and expandable devices that are compressed or expanded by a person's digits to develop and measure the person's grasping force and grasping dexterity. The device can be used in a regiment that allows for quantification, measurement and development of motor skills needed for grasping.

BACKGROUND

Adequate grasping force and grasping dexterity is required for individuals to perform tasks like eating, tying shoe laces and thousands of other everyday tasks. When an individual loses grasping strength or control, their independence and quality of life is severely compromised. Loss of grasping strength and dexterity can result from old age and various other health related causes such as injury or disease. The loss of grasping strength and dexterity may be temporary, as is often the case after a person experiences an injury or orthopaedic surgery and rehabilitation. The speed at which a person can regain proper operation of the hands and digit control after surgery or disease greatly depends on the amount and quality of physical therapy that the individual receives. Personal physical therapists can be very expensive and are not available to each and every patient that requires therapy to regain grasping strength and dexterity.

Thus, patients that cannot afford physical therapy or do not have such services available for one reason or another have to rely on self motivation in order to develop or regain proper operation of the hands after injury. Unfortunately, if the patient is bed ridden he or she will not have the opportunity to tie shoes, wash dishes and the like which can help them to regain dexterity and strength in the hands.

There are several other reasons why an individual may wish to improve his or her grasping strength or grasping dexterity. For example, musicians that use their hands to play instruments may wish to exercise their fingers in environments where practicing their instrument is not feasible or not possible. Rock climbers may wish to improve their grasping strength prior to a climb and surgeons may wish to improve their dexterity to improve their ability to perform delicate operations.

Physical therapy requires the measurement and development of different combinations of finger strength and dexterity. Unfortunately, the available methods to quantify hand and finger functions clinically only measure strength. Dexterity is only measured qualitatively by prior art methods.

Therefore, there is a need for a device that can be used to measure and to improve the grasping strength and grasping dexterity. Preferably, the device is hand-held and can be used in a regiment that measures individual's grasping strength and grasping dexterity.

OBJECTS AND ADVANTAGES

One object of the present invention is to provide a hand-held device that may be used in a therapy to exercise the digits of an individual in order to improve finger strength. The hand-held device allows individuals to remain substantially immobilized while exercising and developing their grasping strength.

It is a further object of the present invention to provide a device, which is flexible and measures grasping dexterity. The device not only allows the individual to develop grasping strength, but also his or her grasping dexterity.

It is yet another object of the current invention to provide a device for developing grasping strength and grasping dexterity, which is inexpensive, can reduce the cost of therapy, and allows individuals to develop grasping strength and grasping dexterity in a variety of environments.

It is also an object of the present invention to provide a device for developing grasping strength and grasping dexterity that yields a quantitative measurement of grasping strength and grasping dexterity.

SUMMARY OF THE INVENTION

These objects and advantages are obtained by providing a hand-held device with a compressible section. In one embodiment of the invention a user holds the device between the palm of his or her hand and applies a force with a finger to compress the device. Through repeated compressions of the device the user can measure and develop grasping strength.

In the preferred embodiment of the invention the device is configured to be held between a finger and a thumb of the same hand. The user compresses the device in a compression direction with the finger and the thumb. In the most preferred embodiment of the invention, the device is also capable of bending or flexing in an off axis direction such that the user must compress the device in a predetermined fashion to achieve successful compression. The ease with which the device is designed to bend in an off axis direction determines the required grasping dexterity that the user must have to successfully compress the device.

To vary the skill level that is required in order to successfully compress the device, a variety of mechanisms are used. For example, different spring stiffnesses and dimensions can be used to increase or decrease the strength and dexterity required to successfully compress the device. Alternatively, flexible elements, hinges and the like can be integrated into the device to make the device more flexible and more difficult to compress. The variety of ways that the device can be modified for different user skill levels and different user goals will become clear in the ensuing examples.

The device can also be configured to operate in an expansion mode such that the user must apply an expansion force to the device in order to develop grasping strength and grasping dexterity. It is also possible that the device requires force to both expand and compress the device. In a particular embodiment of the current invention several springs are attached together by their ends. At the other ends of the springs there are loops for inserting fingers or thumbs. The user inserts his or her fingers and/or thumb into the loops and repeatedly expands the device in various directions to develop and measure grasping strength and grasping dexterity.

All of the embodiments described can be equipped with an automated counter that measures the number of successful or unsuccessful expansions and/or contractions of the device. A series of devices, which require a range of skill levels to operate, can be used in a designed grasping rehabilitation or grasping improvement program for patients, musicians and athletes alike.

BRIEF DESCRIPTION OF FIGURES

FIGS. 5A–5C show sectional side views of various finger pad configuration attached to the ends of springs.

FIGS. 6A–6B show cross-sectional views of a device made in accordance with the current invention with compressible metal spring strips.

FIGS. 7A–7B show cross-sectional views of a device made in accordance with the current invention with compressible metal spring strips and hinges.

DETAILED DESCRIPTION OF THE INVENTION

Figure 1:
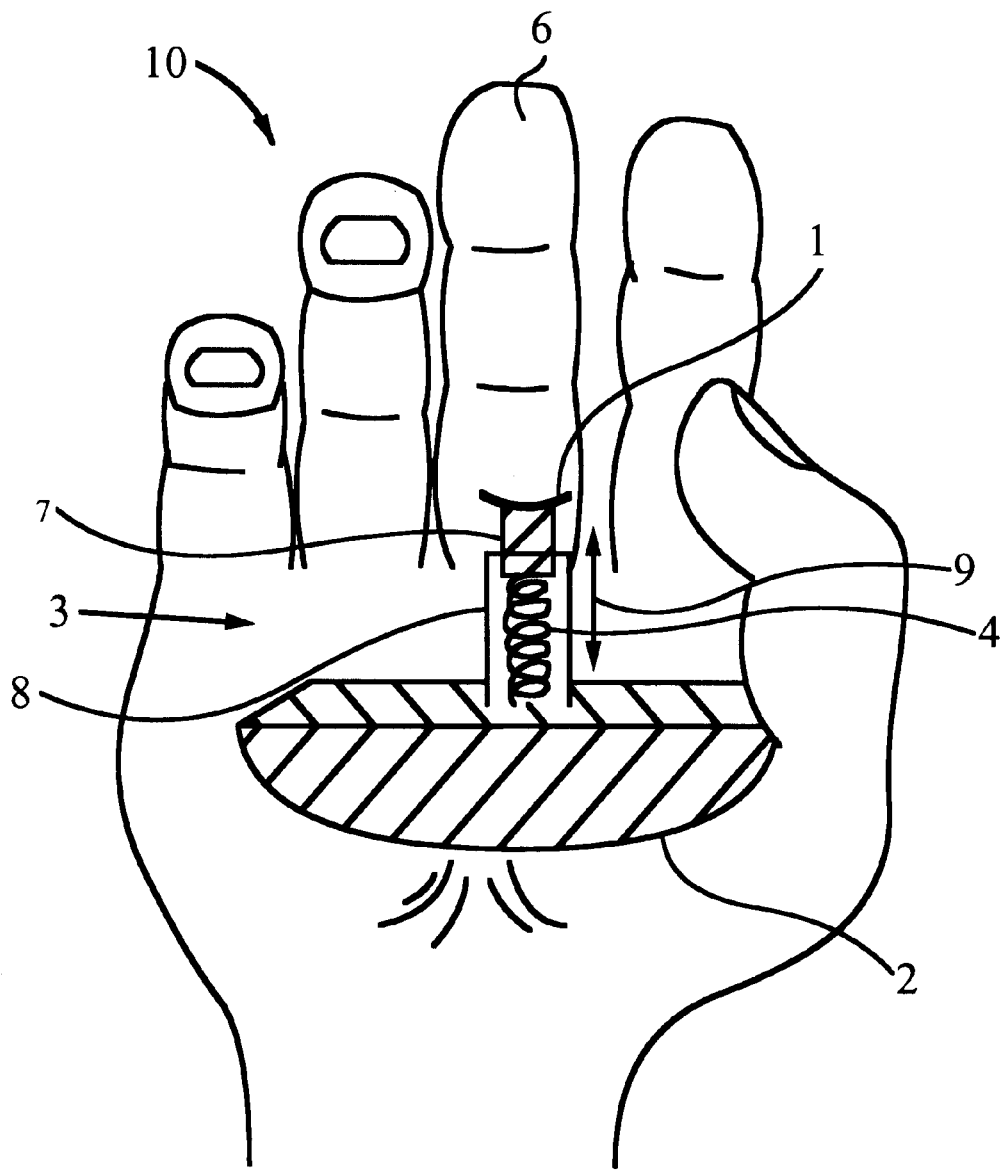
FIG. 1 shows a perspective view of a device made in accordance with the present invention, which is held in the palm of a hand.

FIG. 1 shows a perspective view 10 of a hand-held device 3 made in accordance with the current invention. The device 3, has a finger pad 1 for positioning a finger tip 6 and a palm pad 2, positioned at the opposing end for resting the device in the palm of a hand as shown. The compressible section of the device operates like a piston. A piston portion 7 resists compression because of a compressible element in the form of a spring 4 contained in a spring housing 8. The user places the finger tip 6 on the pad 1 and repeatedly depresses the piston 7 in a linear compression direction 9 such that the piston 7 recedes into the housing 8. The repeated operation of the device 3 as described is used to build up finger strength. A successful compression requires that the piston 7 be depressed to a predetermined depth. The device 3 can have any number of spring strengths tailored to a particular user's ability.

It is preferred that device 3 be configured to be compressed by placing the device between a finger and a thumb and applying the appropriate force along a linear compression direction. It is most preferred that the ends of the device where the finger and thumb are positioned are capable of being displaced in an off axis direction from the linear compression direction. In this way, the user is required to consciously compress the device along the linear compression direction with a certain degree of dexterity. For this purpose coiled springs are particularly useful. The device can be configured to accommodate any number of digits.

Figure 2:
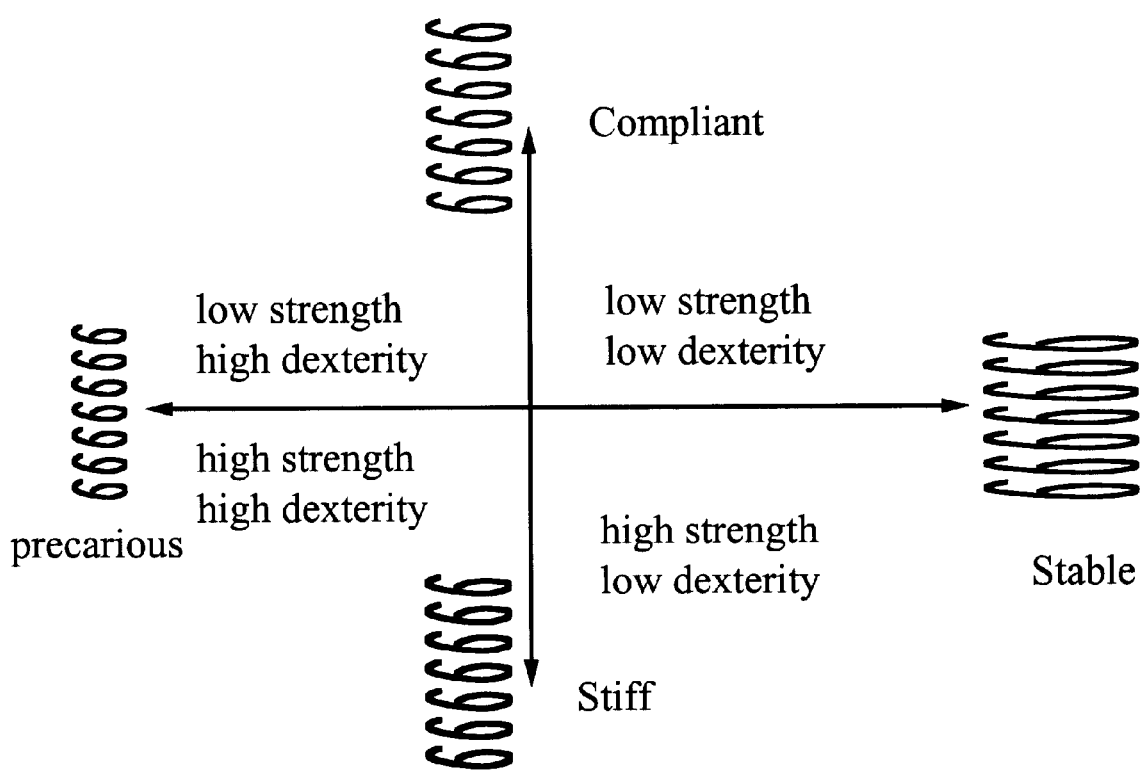
FIG. 2 is a graph showing the spectrum of grasping abilities that can be measures by various springs.

FIG. 2 is used to illustrate variations of compression strength and dexterity required to obtain a linear compression of springs having various physical properties. A compliant spring requires less force to be compressed, while a stiff spring requires more force to be compressed. A wide, short spring is more stable because it requires a less precise alignment of forces to compress, while a narrow, long spring is more precarious because it requires a more precise alignment of forces to compress, thus requiring a greater degree of dexterity to compress. Different types of springs can be used to measure different combinations of finger force and grasping dexterity. For example, a lower degree of finger force and grasping dexterity can be measured with a wide (25 mm diameter), short (12 mm length), compliant (0.1 N/mm stiffness) spring, while a higher degree of finger force and grasping dexterity can be measured with a narrow (8 mm diameter), long (50 mm length), stiff (2 N/mm stiffness) spring.

Figure 3:
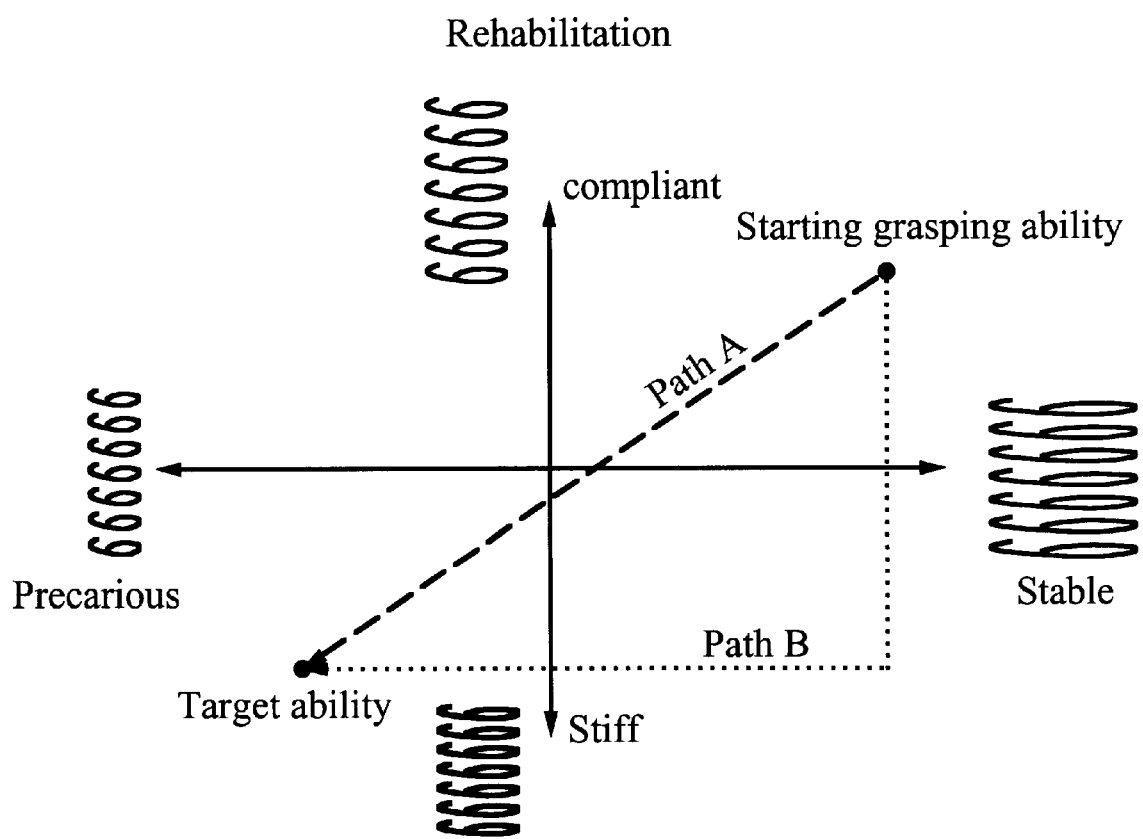
FIG. 3 is a graph showing two rehabilitation paths that can be followed to develop and a patient's grasping strength and grasping dexterity. Path A shows the developments of the strength and dexterity simultaneously. Path B shows the development of the strength first, then dexterity.

For rehabilitation of a patient who has lost some grasping ability, or for training of a person to improve his or her grasping ability, different versions of the device can be used in series. As shown in FIG. 3, a patient or trainee first uses a compliant, stable device and works his or her way up to a precarious, stiff device in Path A. Alternatively, in Path B, a patient or trainee can start with a complaint, stable device, work his or her way up to a stiff, stable device, and then work his or her way up to a stiff, precarious device. The path can be customized for each patient's needs or each trainee's goals.

In addition, the dexterity of the patient or trainee's grasping ability can be quantifiably measured by varying the materials used in construction of the finger pads placed at the ends of the spring. Finger pads with high surface friction, such as sand paper or carpet, can be used to test low dexterity. Finger pads with low surface friction, such as Teflon® or smooth plastic, can be used to test high dexterity. Finger pads with intermediate surface friction, such as wood or cloth, can be used to test intermediate dexterity. Obviously, the more slippery the material used, the more difficult it will be for the patient or trainee to grasp and align the finger pads and then squeeze them together with an opposing force. By varying the texture of the surface, the sensory information of the fingers can be varied and used to quantify and test the influence of finger sensation on grasping ability.

Figure 4A:
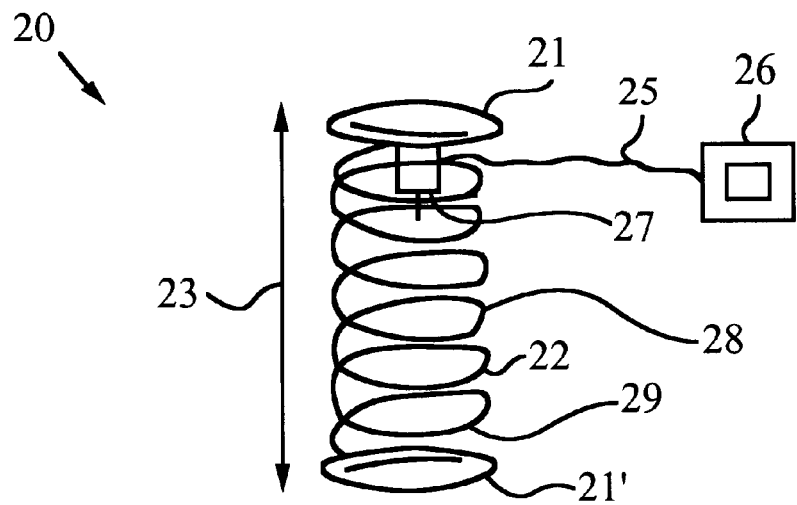
FIGS. 4A–4D show perspective views of a spring device made in accordance with the present invention and its operation.
Figure 4B:
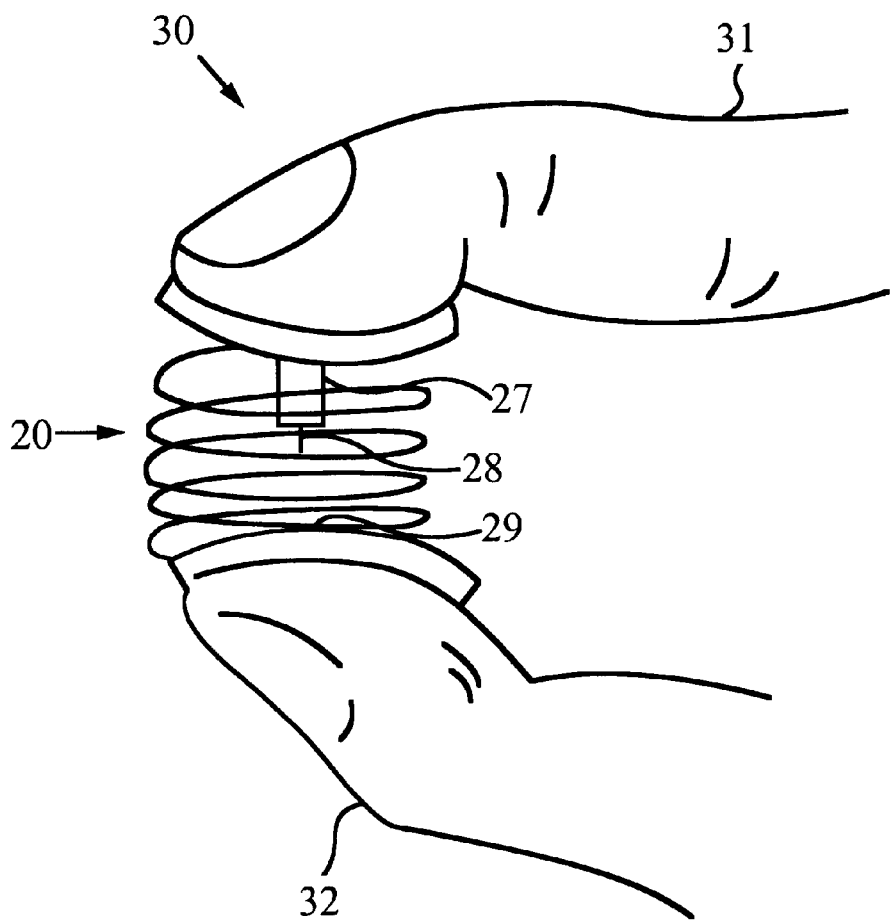
Figure 4C:
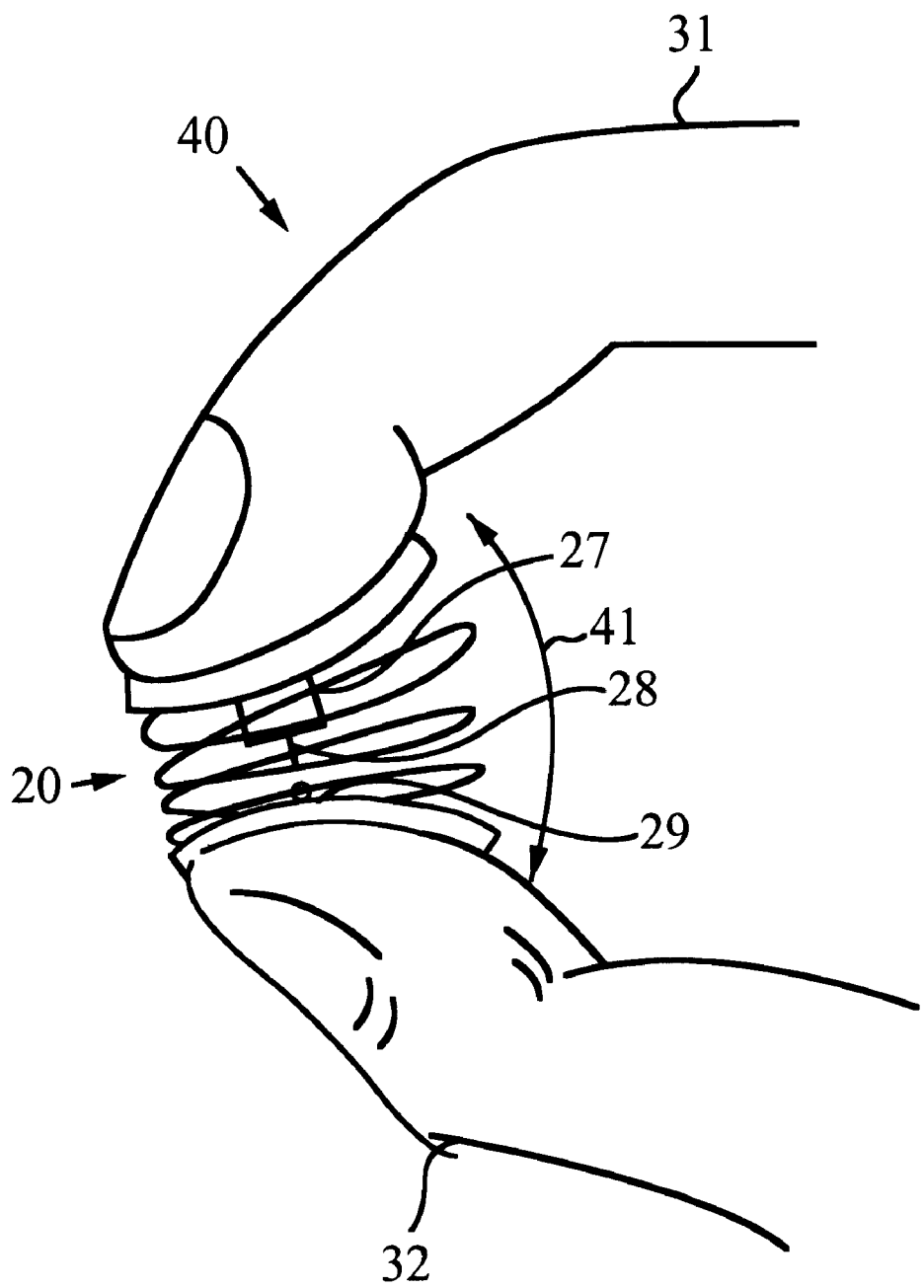
Figure 4D:
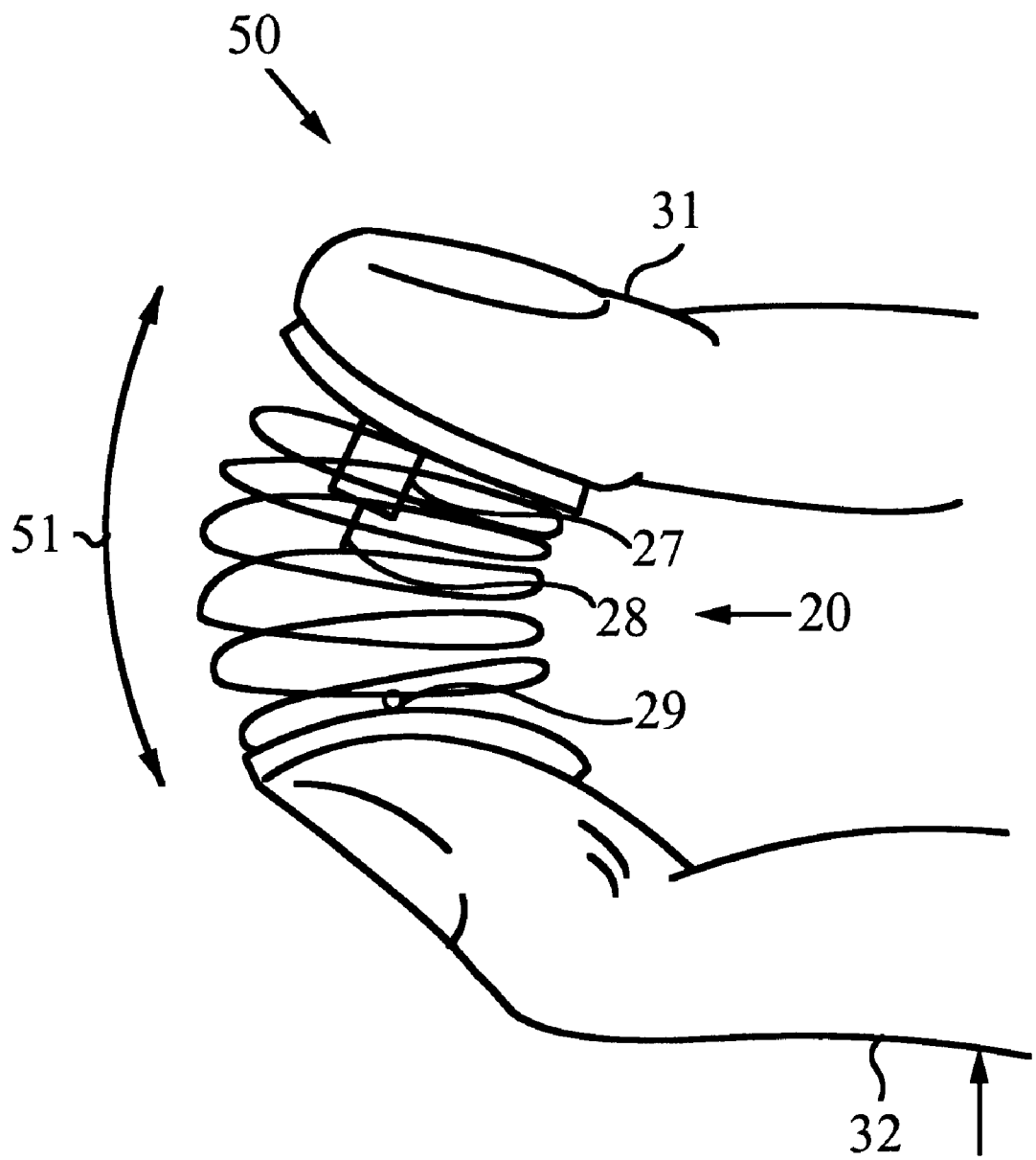

FIG. 4A is a plan side view of an embodiment which can be used to measure and develop grasping force between a thumb and a finger. This embodiment is exemplified by a device 20 which utilizes a spring 28 and the properties of the spring described above. The device 20 has a pad 21 attached to a first end of the spring 28 and a second pad 21' attached to the opposing end of the spring 28. The device 20 is designed for compression along a linear compression direction 23 by applying an appropriate force to the pads 21 and 21'. FIG. 4B shows the device 20 held and compressed between a finger 31 and a thumb 32. The user compresses the device as shown to build up finger strength and finger dexterity. FIGS. 4C and 4D illustrate the improper compression of the device 20, wherein the spring 28 is not compressed along the linear compression direction 23, as required. FIG. 4C shows a plan side view 40, wherein the finger 31 and the thumb 32 are bent inward and apply to the device 20 a force which is not oriented along the linear compression direction 23. Such force is herein called a non-linear force or off axis force, where the axis is taken to be along the linear compression direction 23. The off axis force causes the spring 28 to bend away from the axis and produce a bow 41 in towards the hand (not shown). FIG. 4D shows a plan side view 50 of the device 20 wherein the finger 31 and the thumb 32 are bent outward and apply a non-linear force or off axis force to the device 20 causing the spring 28 to bend away from the axis to produce a bow 51 outwards from the hand (not shown). By counting a number of proper compressions, as illustrated in FIG. 4B, the device is used to measure grasping strength and dexterity.

Again referring to FIG. 4A, the device 20 is equipped with an automated counter 27, such that when the device is compressed correctly and completely the counter 27 registers a compression. The counter 27 is attached to the pad 21, which is attached to a first end of the spring 28. When a contact 22 of the counter 27 contacts a contact point 29 on the pad 21', a compression is registered. It will be obvious to one skilled in the art that there are any number of counter configurations that can be implemented. Again referring to FIG. 4A, the counter 27 can be mechanical, optical, or electrical. In the present case counter 27 is electrical and is attached to an external meter 26 by a connection 25 such that successful compressions can be displayed remotely. Further, the counter 27 can easily be configured to measure both successful and unsuccessful compression and varying degrees thereof. Further, it is understood that all following embodiments can be equipped with a counter such as that which is described above.

Not only can the finger and thumb pads be made of a variety of materials but they can also exhibit a variety of shapes and sizes. FIGS. 5A–C illustrate a few exemplary shapes for finger and thumb pads. In FIG. 5A a pad 52 is a flat surface attached to a compressible element 53; in FIG. 5B, a pad 54 is contoured to make compressing the device easier and the pad 54 is attached to a compressible element 55; and in FIG. 5C a pad 56 is convex and attached to the compressible element 57 providing less contact area with the finger than a flat or contoured pad making successful compressions of the device more difficult. It is also noted that the finger and thumb pads do not have to be directly attached to a compressible element and the compressible element does not need to be a coil spring. The compressible section of the device may be made from a variety of pliable, flexible or resilient materials including plastic, rubber and foam rubber. Alternatively, the compressible section of the device may be made from a combination of different compressible materials.

FIGS. 6A–B show cross-sectional views of an alternative embodiment of the current invention, wherein a device 60 whose compressible section consists of spring strips 63 and 63'. The spring strips 63 and 63' are flexible as shown in FIG. 6B and can be deformed by applying the appropriate force to pads 62 and 64. In FIG. 6B the device 60 is shown in a compressed state.

FIGS. 7A–B illustrate cross-sectional views of yet another embodiment of the current invention. In this embodiment the device 61 has spring strips 65 and 67 that at joined by hinges 69 and 69'. By applying the appropriate pressure to pads 66 and 68, the device 61 is compressed to a state, such as that which is shown in FIG. 7B.

The compressible sections or elements that have been described above return to their original extended position in the absence of an applied force. It is, however, considered to be within the scope of the invention to have a device with a compressible and expandable section that is resistive to both. In this design it is required to have finger and thumb attachments that secure the respective digits of the operator to the device such as to allow the user to apply the appropriate force in both an expansion and a compression direction. For example, the compressible and expandable section can be a pneumatic or friction resistive telescoping element that provides resistance to both compression and expansion.

Figure 8A:
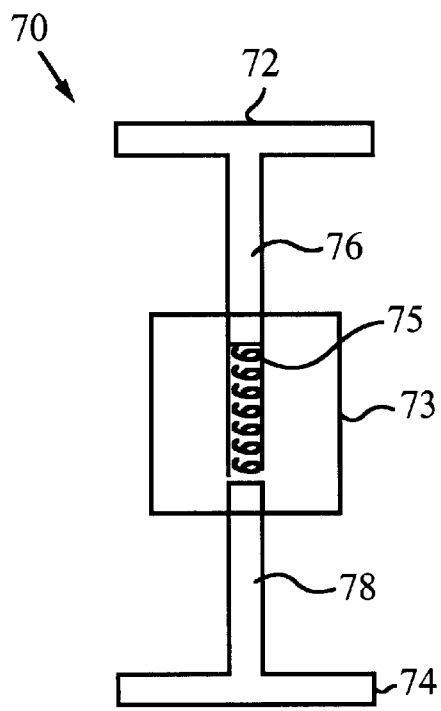
FIGS. 8A–8C show plan side views of a device made in accordance with the present invention, having a compressible spring and a flexible material.
Figure 8B:
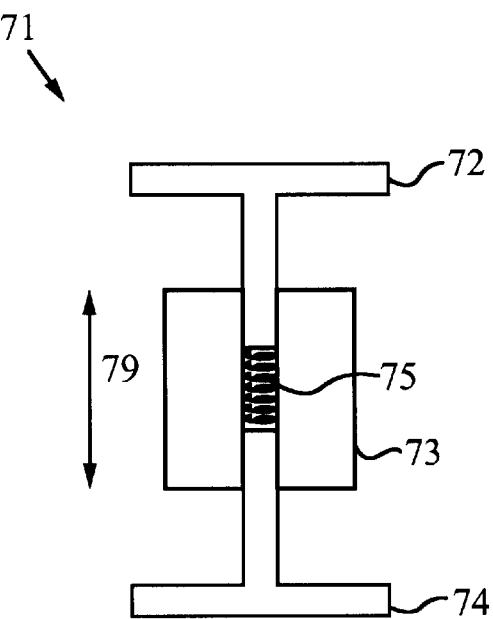
Figure 8C:
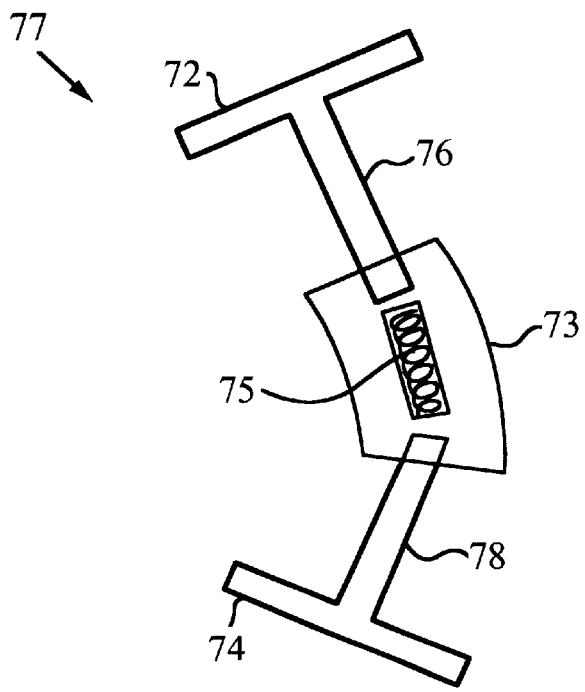

FIGS. 8A–C show an alternative embodiment of the current invention. In FIG. 8A, two stems 76 and 78 are attached to pads 72 and 74 and portions of the stems 76, 78 are lodged within a flexible element 73. The flexible element 73 is preferably a soft material such as flexible rubber or foam rubber. The stems 76 and 78 are capable of being displaced in a linear compression direction 79 as shown in FIG. 8B. The element 73 is flexible along an off axis direction as shown in FIG. 8C. Preferably, there is a spring 75 within the flexible element 73, to provide resistance to compression. However, the device may also operate on pneumatic or resistive principle previously mentioned so that resistance is provided in both the compression and expansion directions. Alternatively, the stems 76 and 78 are securely fastened to the flexible element 73 and spring 75 is absent. The flexible element is sufficiently soft to allow for linear compression of the device when pressure is applied to the pads 72 and 74 without spring 75.

Figure 9:
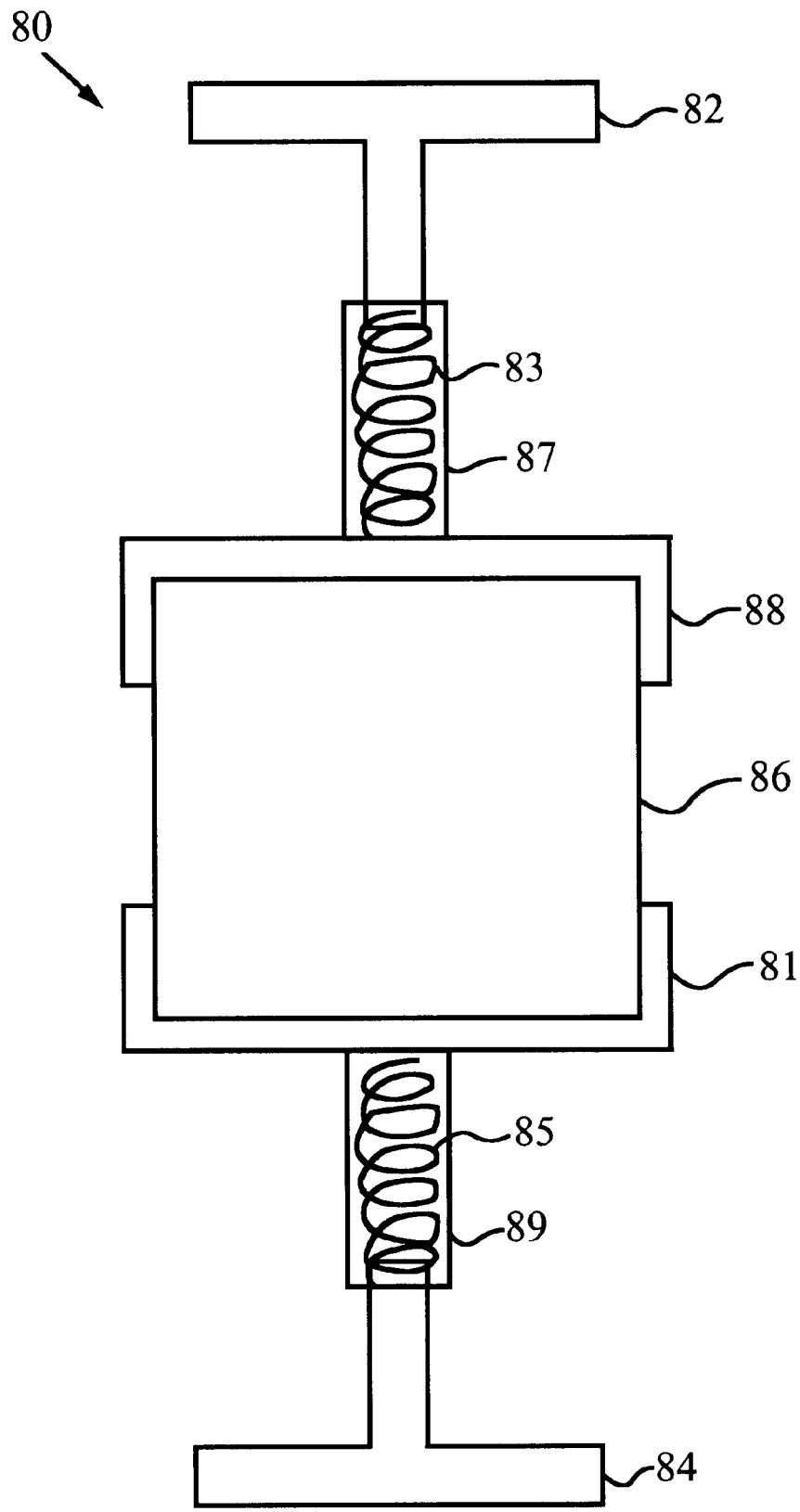
FIG. 9 shows a plan side view of an alternative embodiment of the current invention with two compressible springs and a flexible element between the springs.

FIG. 9 shows a device 80 that has two springs 83 and 85 housed in spring housings 87 and 89, respectively. The springs 83 and 85 are compressible by applying the appropriate pressure to the T-shaped pad sections 82 and 84. In addition to the springs 83, 85 described above, the device has a resilient material 86 held between the springs 83, 85 by supports 88 and 81. The resilient material 86 provides flexibility to the device 80 in the off axis directions whilst the two springs 83 and 85 provide for compressibility of the device in the linear compression direction.

Figure 10:
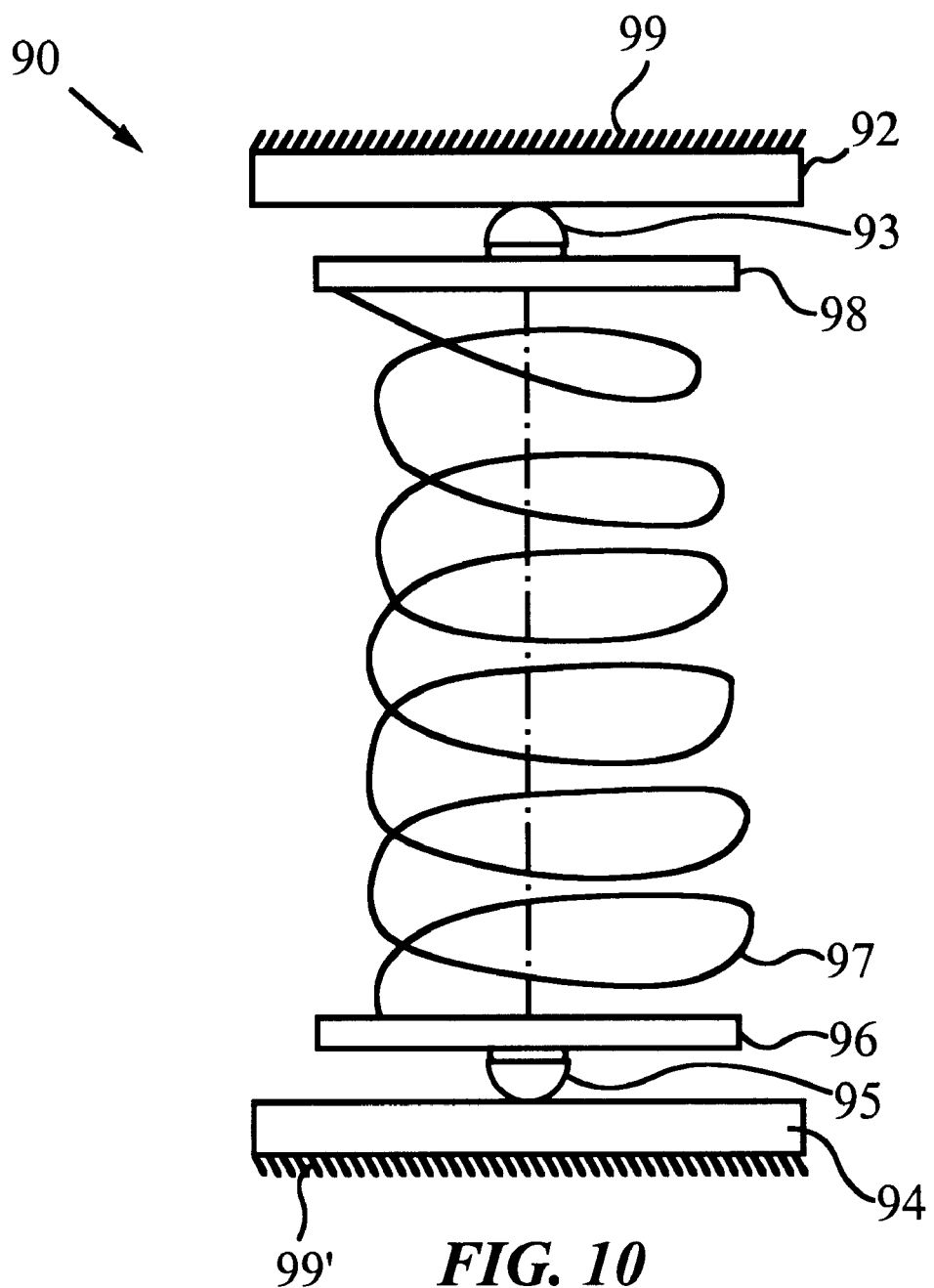
FIG. 10 shows a cross-sectional view of a device for measuring grasping strength and grasping dexterity that has a compressible spring and finger pads attached to the spring through hinged pads.

FIG. 10 shows a cross-sectional view of a device 90 that has a spring 97 positioned between two spring supports 96 and 98. The finger and thumb supports 92 and 94 are attached to the spring supports 96 and 98 through two swiveling ball joint hinges 93 and 95. The ball joint hinges 93 and 95 require a higher degree gripping dexterity from the user to compress the device 90 along a linear compression direction. To aid the user in holding on to the device the finger and a thumb the pads 92 and 94 have roughened gripping surfaces 99 and 99'. The roughened gripping surfaces 99 and 99' may be provided by attaching a cloth or abrasive material to the pads 92 and 94, or by patterning the surface of the pads 92 and 94.

Figure 11:
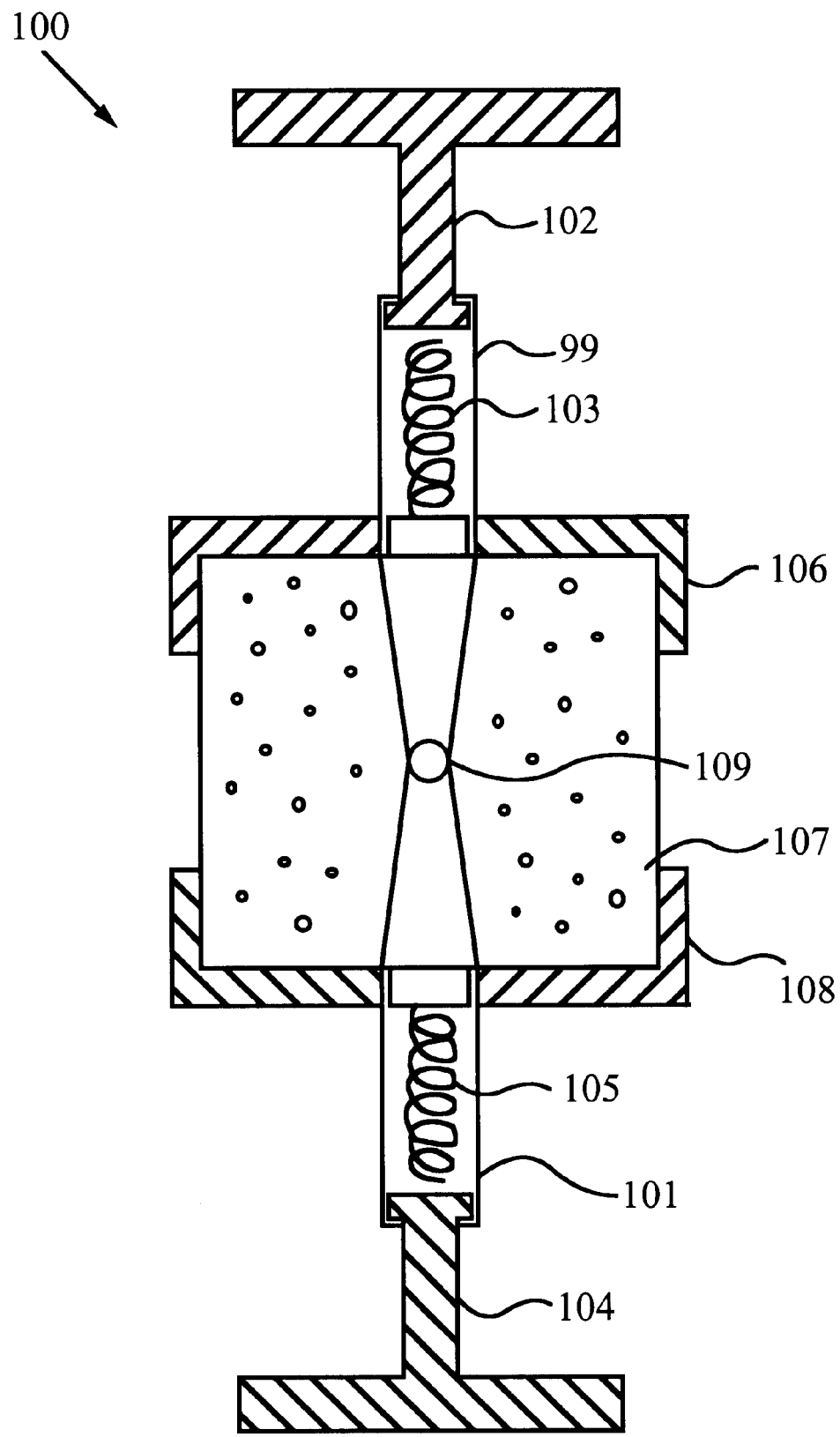
FIG. 11 shows a cross-sectional view of an alternative embodiment of the current invention with two compressible springs, and a flexible element between the springs with a hinging center contained therein.

FIG. 11 shows a cross-sectional view of a device 100 similar to the device shown in FIG. 9. Like the device 80 shown in FIG. 9, device 100 has two springs 103 and 105 housed in spring housings 101 and 101', respectively. The springs 103 and 105 are compressible by applying the appropriate pressure to the T-shaped sections 102 and 104. A resilient material 107 is held between the two springs 103, 105 by supports 106 and 108. The resilient material 107 provides flexibility to the device in the off axis direction. Additionally, the spring housings 101 and 101' are attached together through a pivoting hinge 109 which provides additional flexibility to the device in the off axis direction while the two springs 103 and 105 provide for compressibility of the device in the linear compression direction.

Figure 12:
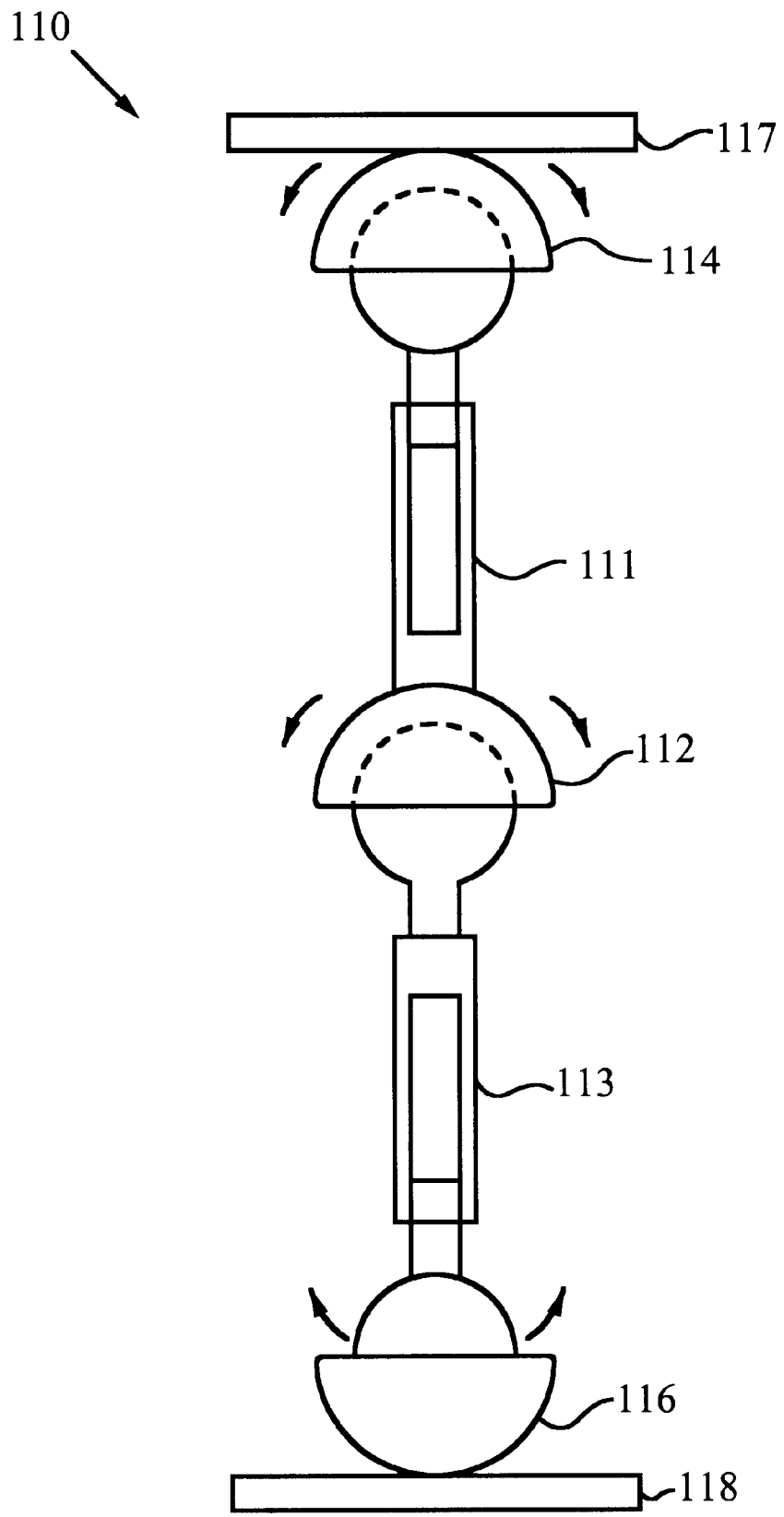
FIG. 12 shows a plan side view of a device with two compressible sections and three pivoting ball joint hinges.

FIG. 12 is a cross-sectional view of a device 110 that has two compressible chambers 111 and 113. The compressible chambers 111 and 113 allow the device 110 to be compressed in a linear compression direction as indicated by arrows C. There are also three pivoting ball joint hinges 114, 112 and 116. The pivoting ball joint hinge 112 allows the device to bend at the center portion of the device 110 in the off axis direction and the pivoting ball joint hinges 114 and 116 allow the pads 117 and 118 pivot. Any number of pivoting and hinging elements can be added to the device 110 to increase the level of difficulty and accuracy required to compress the device along a linear compression direction indicated by arrow C. Thus a series of such devices can be used in a rehabilitation program, wherein the user is given more and more difficult devices to compress as gripping strength and gripping dexterity is improved.

Figure 13:
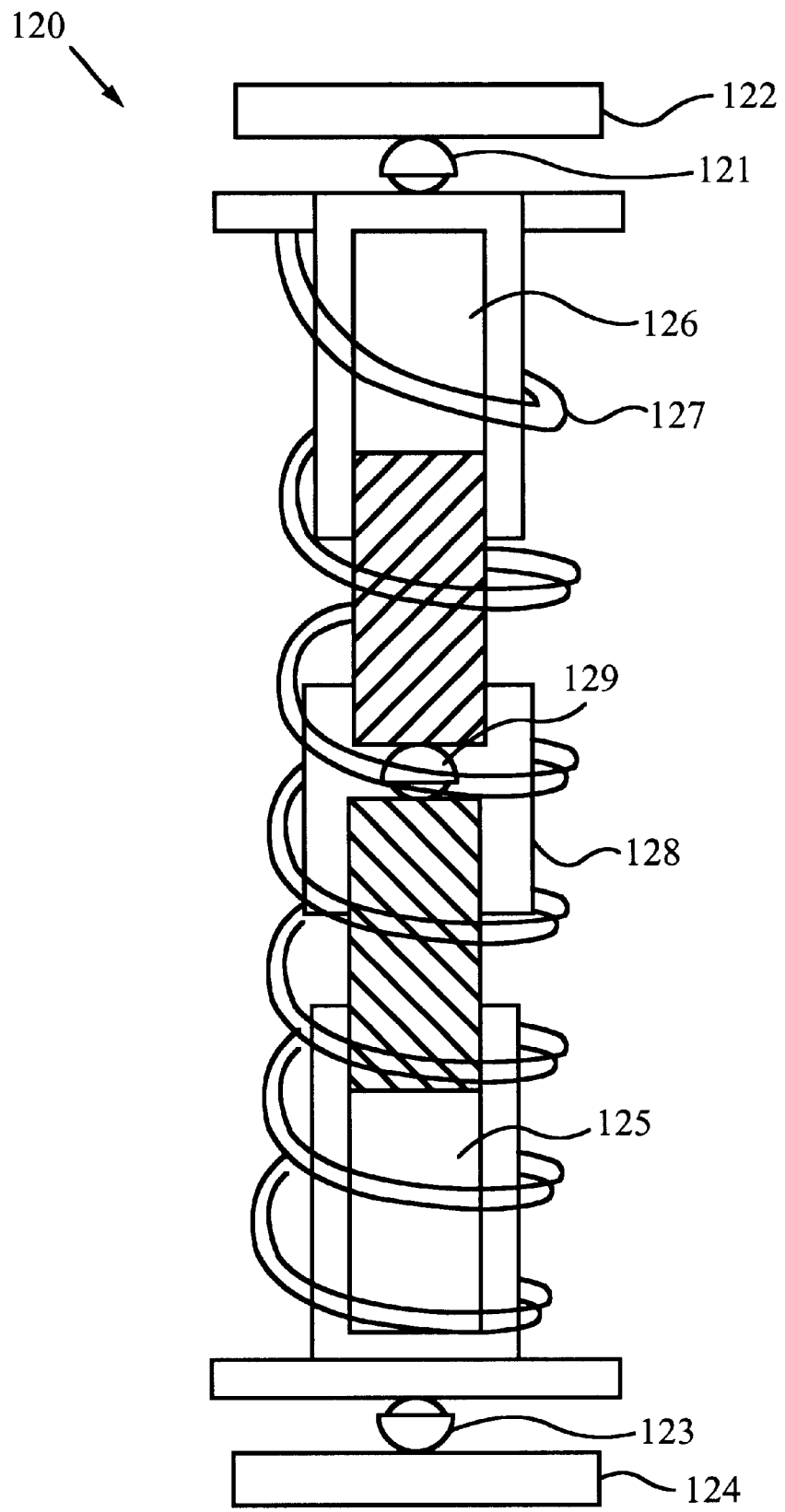
FIG. 13 shows a device for measuring grasping strength and grasping dexterity that utilizes a spring, pivoting ball joint hinges, a compressible section and a flexible material.

In yet another embodiment of the current invention, illustrated in FIG. 13, a device 120 for measuring gripping strength and dexterity utilizes all of the elements described above. The device 120 has compression chambers 126 and 125 that are compressible by applying the appropriate pressure to pads 122 and 124. In addition to the compressible chambers 126 and 125, the device has a coiled spring 127, which also provides resistance to compression of the device along a linear compression direction indicated by arrow C. The pads 122 and 124 are attached to the top portions of the compressible chambers 126 and 125 through pivoting ball joint hinges 121 and 123 that allow the pads 122 and 124 to pivot. In the center portion of the device there is a third pivoting ball joint 129 surrounded by a flexible resilient material 128 that helps control the bending of the device 120 in an off axis direction.

Figure 14:
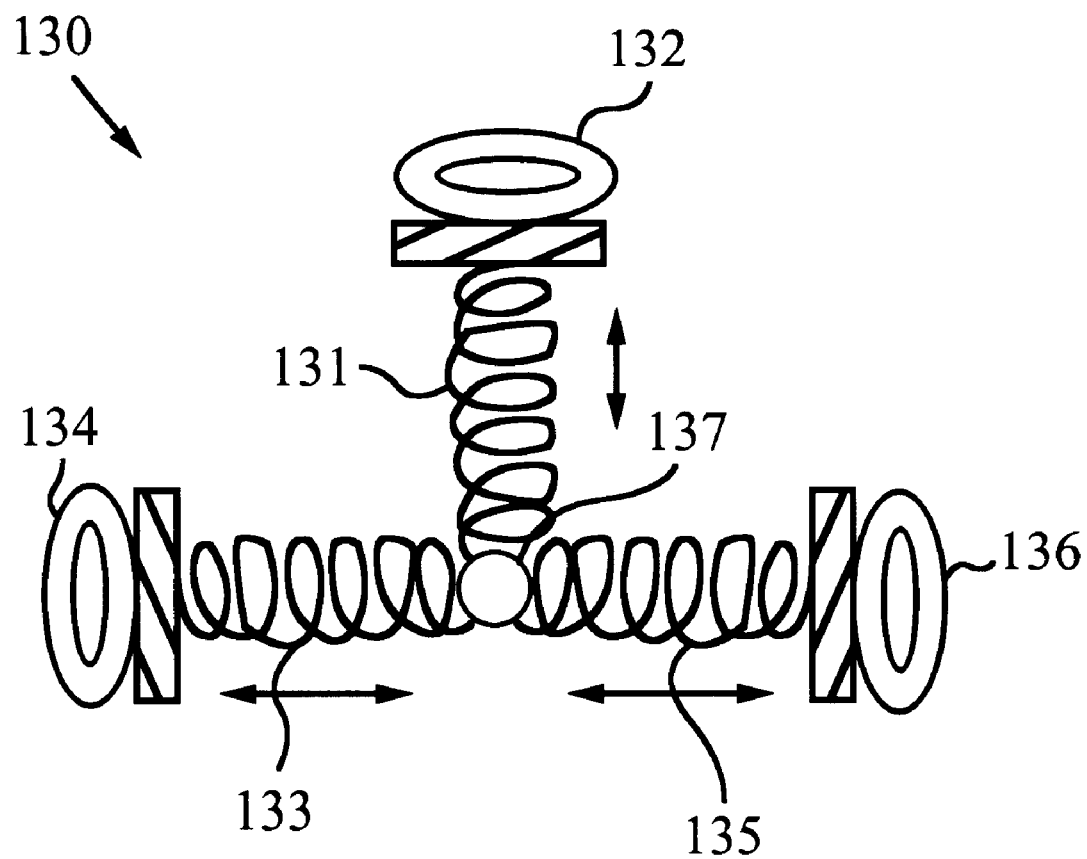
FIG. 14 shows a device for developing grasping strength and grasping dexterity by exercising three digits of a hand.

The devices described above are designed to develop the gripping strength and gripping dexterity through a regimen that exercises one finger or one finger and a thumb. FIG. 14 illustrates an embodiment of the current invention that allows for the development of gripping strength and dexterity through the exercise of three digits. The device 130 has three springs 131, 133 and 135, centrally attached together through an attachment section 137. The finger pads 132, 134 and 136 are equipped with loop supports through which a user inserts three digits. The device is expanded or compressed to help develop gripping strength and gripping dexterity.

Several modifications to the embodiments described are considered to be within the scope of the current invention. For example, all the embodiments described can be equipped with a counter to measure the number of successful or unsuccessful compression and/or expansions of the device. Further, the device can be configured to any number of digits. Therefore, the scope of the current invention is to be determined by the claims and their legal equivalents.

What is claimed is:

1. A device for measuring and developing strength and dexterity in a user, said device comprising:
   a) a compressible section having an extended position, a compressed position, and an axis defining a linear compression direction;
   b) at least one compressible element disposed and laterally unguided with said compressible section, said at least one compressible element being reversibly compressible and having a stiffness and/or damping along said axis defining a user strength required to compress said compressible section from said extended position to said compressed position, and said at least one compressible element having an ability to translate away from said axis defining a user dexterity required to compress said compressible section from said extended position to said compressed position while controlling said translation away from said axis of said at least one compressible element; and
   c) a support for receiving at least one body part of said user, said support being joined to said compressible section such that said user can apply a force to said compressible section to compress said compressible section.

2. The device of claim 1, wherein said at least one compressible element comprises a spring.

3. The device of claim 2, wherein said stiffness along said axis and said ability to translate away from said axis are determined by a length, a width and physical properties of said spring.

4. The device of claim 2, wherein said spring is a coil spring.

5. The device of claim 1, wherein said support comprises at least two pads at opposite ends of said compressible section for receiving at least two body parts of said user.

6. The device of claim 1, wherein said at least one compressible element comprises a resilient material.

7. The device of claim 6, further comprising a support for holding said resilient material.

8. The device of claim 1, wherein said at least one compressible element comprises a compression chamber.

9. The device of claim 1, wherein said compressible section further comprises a joint.

10. The device of claim 9, wherein said joint comprises a pivoting hinge.

11. The device of claim 9, wherein said joint comprises a pivoting ball joint hinge.

12. The device of claim 1, wherein said support comprises at least one pad at one end of said compressible section for receiving at least one body part of said user.

13. The device of claim 1, further comprising a device for monitoring compressions.

14. The device of claim 13, wherein said monitoring device monitors said linear compression direction effected by said user.

15. The device of claim 13, wherein said monitoring device monitors said translation away from said axis during said compression.

16. The device of claim 13, wherein said monitoring device comprises mechanical, optical, inertial or electrical sensors.

17. A device for measuring and developing strength and dexterity in a user, said device comprising:
   a) a compressible section having an extended position, a compressed position, and an axis defining a linear compression direction;
   b) at least one compressible element disposed and laterally unguided with said compressible section, said at least one compressible element being reversibly compressible and having a stiffness and/or damping along said axis defining a user strength required to compress said compressible section from said extended position to said compressed position;
   c) at least one joint disposed in said compressible section, said at least one joint having a resistance against, or propensity for, translating away from said axis and thereby defining a user dexterity required to compress said compressible section from said extended position to said compressed position while controlling said translation of said joint; and
   d) a support for receiving at least one body part of a user of said user, said support being joined to said compressible section such that said user can apply a force to said compressible section to compress said compressible section.

18. The device of claim 17, wherein said at least one compressible element comprises a spring.

19. The device of claim 18, wherein said spring is a coil spring.

20. The device of claim 17, wherein said support comprises at least two pads at opposite ends of said compressible section for receiving at least two body parts of said user.

21. The device of claim 17, wherein said at least one compressible element comprises a resilient material.

22. The device of claim 21, further comprising a support for holding said resilient material.

23. The device of claim 17, wherein said at least one compressible element comprises a compression chamber.

24. The device of claim 17, wherein said joint comprises a pivoting hinge.

25. The device of claim 17, wherein said joint comprises a pivoting ball joint hinge.

26. The device of claim 17, wherein said support comprises at least one pad at one end of said compressible section for receiving at least one body part of said user.

27. The device of claim 17, further comprising a device for monitoring compressions.

28. The device of claim 27, wherein said monitoring device monitors said linear compressions direction effected by said user.

29. The device of claim 27, wherein said monitoring device monitors said translation away of said at least one joint during said compression.

30. The device of claim 27, wherein said monitoring device comprises mechanical, optical, inertial or electrical sensors.

\* \* \* \* \*